United States Patent

Langguth et al.

[11] Patent Number: 6,075,161
[45] Date of Patent: Jun. 13, 2000

[54] PREPARATION OF 3-PENTENOIC ACID ESTERS BY CARBONYLATION OF ALKOXYBUTENES

[75] Inventors: Ernst Langguth, Kirchheim; Regina Schneider, Fussgönheim; Ferdinand Lippert, Bad Dürkheim; Arthur Höhn, Kirchheim, all of Germany

[73] Assignee: BASF Aktiengesellschaft, Ludwigshafen, Germany

[21] Appl. No.: 08/913,510

[22] PCT Filed: Mar. 15, 1996

[86] PCT No.: PCT/EP96/01123

§ 371 Date: Sep. 16, 1997

§ 102(e) Date: Sep. 16, 1997

[87] PCT Pub. No.: WO96/29300

PCT Pub. Date: Sep. 26, 1996

[30] Foreign Application Priority Data

Mar. 22, 1995 [DE] Germany ............. 195 10 324

[51] Int. Cl.$^7$ ................................................. C07C 67/37
[52] U.S. Cl. ............................................................ 560/207
[58] Field of Search ............................................. 560/207

[56] References Cited

U.S. PATENT DOCUMENTS

| | | | |
|---|---|---|---|
| 2,922,822 | 1/1960 | Beach | 260/614 |
| 4,433,164 | 2/1984 | Jenck | 560/207 |
| 4,622,416 | 11/1986 | Hanes et al. | 560/114 |
| 4,894,474 | 1/1990 | Maerkl et al. | 560/206 |
| 5,166,421 | 11/1992 | Bruner, Jr. | 562/522 |
| 5,495,041 | 2/1996 | Sielcken et al. | 560/207 |

FOREIGN PATENT DOCUMENTS

| | | |
|---|---|---|
| 217 407 | 4/1987 | European Pat. Off. . |
| 271 145 | 6/1988 | European Pat. Off. . |
| 284 170 | 9/1988 | European Pat. Off. . |
| 351 616 | 1/1990 | European Pat. Off. . |
| 433 191 | 6/1991 | European Pat. Off. . |
| 478 471 | 4/1992 | European Pat. Off. . |
| 514 288 | 11/1992 | European Pat. Off. . |
| 1110405 | 4/1968 | United Kingdom . |

OTHER PUBLICATIONS

*Dictionary of Organom. Compounds*, vol. 2, 1984, pp. 1484–1544.

Primary Examiner—Johann Richter
Assistant Examiner—Rosalynd Keys
Attorney, Agent, or Firm—Keil & Weinkauf

[57] ABSTRACT

3-Pentenoic esters are prepared by carbonylation of alkoxybutenes in the presence of a catalyst and a solvent at elevated temperature and elevated pressure, by reacting at least one $C_1$–$C_{10}$-alkoxybutene in which the alkoxy group is in the allyl position relative to the double bond with carbon monoxide at from 60 to 140° C. and a carbon monoxide partial pressure in the range from 3 to 30 MPa in the presence of a catalyst based on palladium.

7 Claims, No Drawings

PREPARATION OF 3-PENTENOIC ACID ESTERS BY CARBONYLATION OF ALKOXYBUTENES

The present invention relates to a process for preparing 3-pentenoic esters by carbonylation of alkoxybutenes in the presence of a catalyst and a solvent at elevated temperature and elevated pressure.

EP-A 301 450 and EP-A 351 616 disclose processes for preparing alkyl pentenoates by reacting butadiene with carbon monoxide and alcohols in the presence of cobalt carbonyl complexes and tertiary nitrogen bases. These processes require high pressures of from 120 to 700 bar and form mixtures of 2-, 3- and 4-pentenoic esters.

GB-A 1 110 405 describes a process for preparing pentenoic esters by carbonylation of butadiene in the presence of an alcohol using platinum, palladium and/or nickel catalysts. Here too, high pressures of from 100 to 1000 bar are required.

EP-A 60 734 discloses a process for preparing pentenoic esters by carbonylation of butadiene in the presence of an alcohol, a hydrogen halide and a palladium catalyst at lower pressures around 150 bar. A disadvantage of this process is that a large excess of corrosive hydrogen halide is required (molar ratio of hydrogen halide to palladium is 20–100:1).

According to EP-A 284 170 and EP-A 271 145, pentenoic esters can be prepared by carbonylation of butadiene in the presence of alcohols using palladium compounds, phosphines and acids. This does not give the 3-pentenoic ester in pure form, but in admixture with its isomers.

Another way of preparing β,γ-unsaturated esters is described in U.S. Pat. No. 4,622,416. Carbonylation of allyl ethers catalyzed by nickel, cobalt or iron halides gives the esters. A disadvantage of this process is the formation of product mixtures. The carbonylation of 8-methoxy-1,6-octadiene gives not only methyl 3,8-nonadienoate but also three cyclic carboxylic acid compounds. Satisfactory selectivities (maximum 91%) can only be obtained at a pressure above 170 bar and a temperature of 150° C. Under these conditions the catalyst loss resulting from formation of volatile nickel compounds is very high.

EP-A 217 407 describes the carbonylation of allyl ethers with $PdCl_2/CuCl_2$ catalysis to give unsaturated esters. Here, large amounts of tetrabutylammonium chloride (25 mol % based on starting material) are added to the reaction mixture for extraction of the product. This addition leads to extensive precipitation of metallic palladium.

EP-A 514 288, EP-A 478 471 and EP-A 433 191 disclose the double carbonylation of 1,4-butenediols and 1,4-dialkoxybutenes to give dehydroadipic acid (diesters) using palladium compounds and chlorides such as alkali metal, alkaline earth metal or quaternary ammonium or phosphonium halides. These processes require a large excess of chloride (typical molar ratios of Pd to chloride of from 1:17 to 1:27) or else large amounts of $PdCl_2$ of about 20 mol %, based on the starting material.

It is an object of the present invention to provide a process for preparing 3-pentenoic esters containing a very low proportion of isomeric 2- and 4-pentenoic esters by carbonylation of alkoxybutenes in the presence of a catalyst based on palladium under mild conditions.

We have found that this object is achieved by a process for preparing 3-pentenoic esters by carbonylation of alkoxybutenes in the presence of a catalyst and a solvent at elevated temperature and elevated pressure, by reacting at least one $C_1$–$C_{10}$-alkoxybutene in which the alkoxy group is in the allyl position relative to the double bond with carbon monoxide at from 60 to 140° C. and a carbon monoxide partial pressure in the range from 3 to 30 MPa in the presence of a catalyst based on palladium.

In addition, we have found a homogeneous catalyst system in which no catalyst deactivation occurs as a result of palladium precipitation if the carbonylation is carried out in the additional presence of quaternary ammonium or phosphonium salts or specific phosphines.

The starting materials used in the process of the invention include at least one $C_1$–$C_{10}$-alkoxybutene, preferably a $C_1$–$C_4$-alkoxybutene, in which the alkoxy group is in the allyl position relative to the double bond. Preference is given to 3-methoxy-1-butene, 3-ethoxy-1-butene, 3-n-propoxy-1-butene, 3-n-butoxy-1-butene, trans-1-methoxy-2-butene, trans-1-ethoxy-2-butene, trans-1-n-propoxy-2-butene, trans-1-n-butoxy-2-butene, cis-1-methoxy-2-butene, cis-1-ethoxy-2-butene, cis-1-n-propoxy-2-butene, cis-1-n-butoxy-2-butene, and mixtures thereof, particularly a mixture of 3-methoxy-1-butene, trans-1-methoxy-2-butene and cis-1-methoxy-2-butene.

The starting compounds can be prepared according to U.S. Pat. No. 2,922,822 by acid-catalyzed alcohol addition to butadiene.

The catalyst used according to the invention is a catalyst based on palladium. Preference is given to using palladium compounds in the oxidation states 0, +1 or +2, which can be present as palladium salts or palladium complexes, in particular $PdCl_2$, $PdCl_2$-(benzonitrile)$_2$, $PdCl_2$(acetonitrile)$_2$, $Pd(OAc)_2$, bis(allylchloropalladium) complexes and dichlorodiphosphinepalladium complexes. Such compounds are known to those skilled in the art, for example from Dictionary of organometallic Compounds, Vol. 2, 1984, Chapman and Hall, pp. 1484–1544.

The molar ratio of palladium compound to alkoxybutene (or the sum of the moles of the alkoxybutenes used) is usually in the range from 0.1:1 to 10:1, preferably from 0.5:1 to 5:1.

In a preferred embodiment, the activity and/or the stability of the palladium catalyst can be increased by addition of chlorides, acids, nitrogen-containing or phosphorus-containing ligands (hereinafter referred to altogether as additives). Chlorides used are preferably alkali metal, alkaline earth metal, transition metal, quaternary ammonium and phosphonium chlorides such as lithium, sodium, potassium chloride, preferably sodium chloride, magnesium, calcium, strontium, barium dichloride, preferably calcium dichloride, copper dichloride, silver chloride, gold trichloride, preferably copper dichloride, and also compounds of the general formula $R^1R^2R^3R^4NCl$, $R^1R^2R^3R^4PCl$ or $(R^5)_3N=P=N(R^5)_3$, where $R^1$ to $R^4$ are identical or different and are aliphatic groups having from 1 to 10 carbon atoms, preferably from 4 to 8 carbon atoms, and/or unsubstituted or substituted aryl groups, $R^5$ is an aryl group having 6–10 carbon atoms which is unsubstituted or substituted by alkyl groups, alkoxy groups or alkoxycarbonyl groups having 1–4 carbon atoms or by halogen, particular preference being given to using tetrabutylammonium chloride, tetrabutylphosphonium chloride and bis(triphenylphosphine) imimium chloride.

Acids preferably used are inorganic and organic protic acids such as hydrochloric acid, sulfuric acid, phosphoric acid, tetrafluoroboric acid or sulfonic acids such as methanesulfonic acid and p-toluenesulfonic acid or Lewis acids such as boron trifluoride-diethyl ether complex and aluminum trichloride.

Phosphorus compounds preferably used are phosphines having the general formula $R^6R^7R^8P$, where $R^6$ to $R^8$ are identical or different and are aliphatic groups having from 1 to 10 carbon atoms, preferably from 4 to 8 carbon atoms, unsubstituted or substituted aryl or unsubstituted or substituted heteroaryl groups having from 6 to 10 carbon atoms, preferably phenyl, pyridyl and pyrimidyl groups. Examples which may be mentioned are triphenylphosphine, tricyclohexylphosphine, tris(2-methoxyphenyl)phoshine, tris(3-methoxyphenyl)phosphine, tris(4-methoxyphenyl) phosphine and 2-diphenylphosphinopyridine.

Other phosphorus compounds which can be used are multidentate chelate ligands such as bis(diphenylphosphino) methane, 1,2-bis-(diphenylphosphino)ethane, 1,3-bis (diphenylphosphino)propane, 1,4-bis(diphenylphosphino) butane and bis(di-tert-butylphosphino)methane.

In general, the molar ratio of additive to palladium is chosen within the range from 0.1 to 10, preferably from 0.5 to 4.

According to the invention, the carbonylation is carried out at from 60 to 140° C., preferably from 80 to 120° C., and at a carbon monoxide partial pressure in the range from 3 to 30 MPa, preferably from 5 to 15 MPa.

Furthermore, the carbonylation can be carried out batchwise or continuously.

In addition, the carbonylation can be carried out in the presence of a solvent, with the weight ratio of solvent to alkoxybutene(s) generally being chosen in the range from 0.5:1 to 15:1, preferably from 2:1 to 10:1.

Solvents used are aliphatic, cycloaliphatic or aromatic alcohols having from one to ten carbon atoms, preferably from one to four carbon atoms, preference being given to using alcohols ROH whose RO radical corresponds to the $C_1$–$C_{10}$-alkoxy radical of the alkoxybutene used, preferably methanol, ethanol, n-propanol and n-butanol;

aliphatic or aromatic nitriles having from two to ten carbon atoms, preferably benzonitrile, acetonitrile, propionitrile;

ureas having from five to fifteen carbon atoms, preferably tetramethylurea, dimethylethyleneurea, dimethylpropyleneurea;

acid amides having from three to ten carbon atoms, preferably dimethylformamide, dibutylformamide, dimethylacetamide, N-methyl-2-pyrrolidone;

carbamic esters having from four to thirteen carbon atoms such as 3-methyl-2-oxazolidinone;

hydrocarbons having from five to ten carbon atoms such as benzene and toluene;

ethers having from two to sixteen carbon atoms such as methyl tert-butyl ether, diphenyl ether;

and mixtures thereof.

The 3-pentenoic esters which can be prepared according to the invention are important intermediates for preparing, for example, adipic acid, caprolactam and caprolactone and also their polymers and copolymers such as polyamide-6 and polyamide-66.

The advantages of the process of the invention compared with processes of the prior art are that high pressures, ie. pressures of more than 30 MPa, can be avoided, that high yields are achieved, that 3-pentenoic esters are obtained in high isomeric purity, that isomer mixtures of alkoxybutenes can be used, that the process can also be carried out continuously and that the catalyst can be recycled without great loss in activity.

EXAMPLES

In all examples, the yields were determined by gas chromatography. No 4-pentenoic ester could be detected. In the Examples 1 to 19, less than 2% of 2-pentenoic ester, based on the respective 3-pentenoic ester, was formed.

Example 1

A mixture of 61.48 mmol of 3-methoxy-1-butene, 48.72 mmol of trans-1-methoxy-2-butene, 5.8 mmol of cis-1-methoxy-2-butene, 5.6 mmol of $PdCl_2$ and 45 g of methanol were treated at room temperature with 10 MPa of carbon monoxide in a 300 ml autoclave. The mixture was subsequently heated to 80° C. and stirred for 5 hours at this temperature and the pressure which was established (12 MPa). It was then cooled to room temperature and the pressure was brought to atmospheric pressure. The yield of methyl 3-pentenoate was 60%.

Examples 2 to 4

A mixture of 53.0 mmol of 3-methoxy-1-butene, 42.0 mmol of trans-1-methoxy-2-butene, 5.0 mmol of cis-1-methoxy-2-butene, 2.5 mmol of $PdCl_2$ and 40 g of a solvent (see Table 1) was treated at room temperature with 5 MPa of carbon monoxide in a 300 ml autoclave. The mixture was subsequently heated (for temperature see Table 1) and stirred for 5 hours at this temperature and a pressure of 10 MPa. It was then cooled to room temperature and the pressure was brought to atmospheric pressure. The yield of methyl 3-pentenoate is likewise shown in Table 1.

TABLE 1

| Example | Solvent | Temperature [° C.] | Yield [%] |
|---|---|---|---|
| 2 | dimethylpropyleneurea | 80 | 57 |
| 3 | benzonitrile | 100 | 61 |
| 4 | MeOH/benzonitrile (1:1) | 100 | 61 |

Examples 5 to 18

A mixture of 53.0 mmol of 3-methoxy-1-butene, 42.0 mmol of trans-1-methoxy-2-butene, 5.0 mmol of cis-1-methoxy-2-butene, 2.5 mmol of $PdCl_2$, from 2.5 to 10 mmol of an additive (see Table 2) and 40 g of a solvent (see Table 2) was treated at room temperature with 10 MPa of carbon monoxide in a 300 ml autoclave. The mixture was subsequently heated to 100° C. and stirred for 5 hours at this temperature and at the pressure which was established (<13 MPa). It was then cooled to room temperature and the pressure was brought to atmospheric pressure. The yield of methyl 3-pentenoate is likewise shown in Table 2.

TABLE 2

| Ex. | Solvent | Additive (mol per mol of Pd) | Yield [%] |
|---|---|---|---|
| 5 | benzonitrile | $CuCl_2$ (1) | 75 |
| 6 | " | $AlCl_3$ (1) | 72 |
| 7 | " | $Bu_4PCl$ (2) | 39 |
| 8 | " | $Bu_4NCl$ (1) | 60 |
| 9 | " | $Ph_2PPy$, MSA (1/1) | 74 |
| 10 | " | $Ph_2PPy$, MSA (4/4) | 56 |
| 11 | NMP | $Bu_4NCl$ (1) | 71 |
| 12 | " | $P(o\text{-}CH_3OC_6H_4)_3$ (1) | 77 |
| 13 | " | $Ph_2PPy$, p-TosOH (4/4) | 63 |
| 14 | 3-methyl-2-oxazolidinone | $Ph_2PPy$, MSA (4/4) | 58 |
| 15 | " | $Bu_4NCl$ (1) | 73 |
| 16 | tetramethylurea | $Ph_2PPy$, MSA (4/4) | 58 |
| 17 | dimethylpropyleneurea | $Ph_2PPy$, MSA (4/4) | 57 |
| 18 | dimethylacetamide | $Bu_4NCl$ (1) | 64 |

TABLE 2-continued

| Ex. | Solvent | Additive (mol per mol of Pd) | Yield [%] |
|---|---|---|---|

NMP = N-methylpyrrolidone
Ph$_2$PPy = 2-diphenylphosphinopyridine
MSA = methylsulfonic acid Example 19

A mixture of 26.5 mmol of 3-methoxy-1-butene, 21 mmol of trans-1-methoxy-2-butene, 2.5 mmol of cis-1-methoxy-2-butene, 2.5 mmol of Pd(OAc)$_2$, 5 mmol of 1,4-bis (diphenylphosphino)butane and 50 g of toluene was treated at room temperature with 10 MPa of carbon monoxide in a 300 ml autoclave. The mixture was subsequently heated to 110° C. and stirred for 20 hours at this temperature and at the pressure which was established (11 MPa). It was then cooled to room temperature and the pressure was brought to atmospheric pressure. The yield of methyl 3-pentenoate. was 35%.

Example 20

5.25 g/h of a solution of the composition 48.0% by weight of methoxybutene isomer mixture (molar ratio 3-methoxy-1-butene: trans-1-methoxy-2-butene: cis-1-methoxy-2-butene=49:45:6) in N-methyl-2-pyrrolidone (NMP) and 11.9 g/h of catalyst solution of the composition 2.20% by weight of PdCl$_2$ and 7.36% by weight of Bu$_4$NCl hydrate in NMP plus 6 l/h of gaseous CO were continuously fed into an autoclave (volume: 94 ml) fitted with magnetic stirrer and thermostated to 100° C. in an oil bath. The pressure was kept constant at 100 bar. 21.0 g/h of liquid product was taken off continuously via a regulator valve. The yield of methyl 3-pentenoate was 73.6% at a conversion of 85.5%. Methyl 2-pentenoate was formed in a yield of 5.1%. No Pd precipitation was visible in the autoclave. 99% by weight of the palladium used could be detected in dissolved form in the liquid reaction product.

Example 21

The experiment of Example 19 was repeated, except that 9.10 g/h of a solution of the composition 48.8% by weight of methoxybutene isomer mixture (molar ratio 3-methoxy-1-butene: trans-1-methoxy-2-butene: cis-1-methoxy-2-butene=45:50:5) in NMP and 20.6 g/h of catalyst solution of the composition 2.20% by weight of PdCl$_2$ and 7.36% by weight of Bu$_4$NCl hydrate in NMP were used. The yield of methyl 3-pentenoate was 69.4% at a conversion of 78.9%. Methyl 2-pentenoate was formed in a yield of 3.4%. No Pd precipitation was visible in the autoclave. The palladium used could be found quantitatively in dissolved form in the liquid reaction product.

The product and unreacted starting material were separated by Sambay distillation (100° C., 30 mbar) and the catalyst-containing distillation residue was reused in place of a fresh catalyst solution. After recycling the catalyst solution three times in the manner just described, a yield of methyl 3-pentenoate of 69.0% and a yield of methyl 2-pentenoate of 3.4% were achieved at a conversion of 77.9%.

We claim:

1. A process for preparing 3-pentenoic esters by carbonylation of alkoxybutenes in the presence of a catalyst and a solvent at elevated temperature and elevated pressure, which comprises reacting at least one C$_1$–C$_{10}$-alkoxybutene in which the alkoxy group is in the allyl position relative to the double bond with carbon monoxide at a temperature in the range from 60 to 140° C. and a carbon monoxide partial pressure in the range from 3 to 30 MPa in the presence of a catalyst based on palladium, wherein the carbonylation is carried out in the additional presence of an additive which increases the activity and/or stability of the palladium catalyst selected from the group consisting of chlorides, inorganic acids, and Lewis acids at a molar ratio of additive to catalyst of from 0.1 to 10 wherein the molar ratio of catalyst to alkoxybutene is from 0.1:1 to 10:1 and wherein the process yields essentially no 4-pentenoic ester and less than 2% of 2-pentenoic ester based on the respective 3-pentenoic ester.

2. A process as claimed in claim 1, wherein a mixture of trans-1-methoxy-2-butene and cis-1-methoxy-2-butene is used.

3. A process as claimed in claim 1, wherein a mixture of 3-methoxy-1-butene, trans-1-methoxy-2-butene and cis-1-methoxy-2-butene is used.

4. The process of claim 1 wherein the molar ratio of additive to catalyst is from 0.5 to 4.

5. A process for preparing 3-pentenoic esters by carbonylation of alkoxybutenes in the presence of a catalyst and a solvent at elevated temperature and elevated pressure, which comprises reacting at least one C$_1$–C$_{10}$-alkoxybutene in which the alkoxy group is in the allyl position relative to the double bond with carbon monoxide at a temperature in the range from 60 to 140° C. and a carbon monoxide partial pressure in the range from 3 to 30 MPa in the presence of a catalyst consisting essentially of a catalyst based on palladium wherein essentially no further additive which increases the activity and/or stability of the palladium catalyst is present and wherein the process yields essentially no 4-pentenoic ester and less than 2% of 2-pentenoic ester based on the respective 3-pentenoic ester.

6. A process as claimed in claim 5, wherein a mixture of trans-1-methoxy-2-butene and cis-1-methoxy-2-butene is used.

7. A process as claimed in claim 5, wherein a mixture of 3-methoxy-1-butene, trans-1-methoxy-2-butene and cis-1-methoxy-2-butene is used.

* * * * *